United States Patent
Schmidt

(10) Patent No.: US 9,217,693 B2
(45) Date of Patent: Dec. 22, 2015

(54) NANOSTRUCTURED FLUID SAMPLING DEVICE

(75) Inventor: Howard Khan Schmidt, Dhahran (SA)

(73) Assignee: SAUDI ARABIAN OIL COMPANY (SA)

( * ) Notice: Subject to any disclaimer, the term of this patent is extended or adjusted under 35 U.S.C. 154(b) by 399 days.

(21) Appl. No.: 13/610,320

(22) Filed: Sep. 11, 2012

(65) Prior Publication Data

US 2013/0152708 A1 Jun. 20, 2013

Related U.S. Application Data

(60) Provisional application No. 61/533,447, filed on Sep. 12, 2011.

(51) Int. Cl.
| | |
|---|---|
| G01N 1/22 | (2006.01) |
| G01N 1/10 | (2006.01) |
| E21B 49/08 | (2006.01) |
| G01N 1/12 | (2006.01) |
| G01N 1/14 | (2006.01) |

(52) U.S. Cl.
CPC G01N 1/10 (2013.01); E21B 49/08 (2013.01); G01N 1/12 (2013.01); G01N 2001/1093 (2013.01); G01N 2001/149 (2013.01)

(58) Field of Classification Search
CPC ..... G01N 2001/028; G01N 1/02; G01N 1/10; G01N 1/22; G01N 1/08
USPC .......................................................... 73/864
See application file for complete search history.

(56) References Cited

U.S. PATENT DOCUMENTS

| | | | | |
|---|---|---|---|---|
| 3,484,342 A | * | 12/1969 | Fuerst et al. ................... 205/202 |
| 3,961,111 A | * | 6/1976 | Smith ........................ 427/419.2 |
| 4,368,107 A | * | 1/1983 | Maejima et al. .............. 205/150 |
| 4,465,562 A | * | 8/1984 | Kadooda ....................... 427/409 |
| 6,602,567 B2 | * | 8/2003 | Han .............................. 428/36.9 |
| 7,432,371 B2 | * | 10/2008 | Kriesel et al. ................. 540/474 |
| 7,595,368 B2 | * | 9/2009 | Kriesel et al. ................. 526/201 |
| 8,449,603 B2 | * | 5/2013 | Weber et al. ................. 623/1.48 |
| 2005/0079551 A1 | * | 4/2005 | Mizuno et al. ................ 435/7.1 |
| 2005/0112171 A1 | | 5/2005 | Tang et al. |
| 2007/0281021 A1 | | 12/2007 | McKinney et al. |
| 2010/0134948 A1 | * | 6/2010 | Park et al. ..................... 361/286 |

FOREIGN PATENT DOCUMENTS

WO 2005/062986 A2 7/2005

OTHER PUBLICATIONS

PCT Notification of Transmittal of the International Search Report and the Written Opinion of the International Searching Authority, or the Declaration; dated Jul. 1, 2013; International Application No. PCT/US2012/054551; International File Date: Sep. 11, 2012.

* cited by examiner

*Primary Examiner* — Hezron E Williams
*Assistant Examiner* — Rodney T Frank
(74) *Attorney, Agent, or Firm* — Bracewell & Giuliani LLP; Constance Gall Rhebergen

(57) ABSTRACT

Disclosed is a nanostructured device for the in-situ capture of fluid samples at selectable times. The device includes a porous anodic alumina substrate having a plurality of elongated pores and an erodible capping material covering the pores. The device is transported into and through a geological reservoir while suspended in an injected carrier fluid. The device can optionally include a polymeric coating to improve minimize flocculation and sedimentation and prevent adhesion to surfaces in the reservoir. Upon erosion of the capping material, the fluids can diffuse into and fill each exposed pore. After a period of time, the hot water of the medium causes swelling and closure of the pore, effectively locking the fluid sample inside the pore. The device may be retrieved and analyzed to determine the composition and properties of the captured fluids.

14 Claims, No Drawings

NANOSTRUCTURED FLUID SAMPLING DEVICE

RELATED APPLICATIONS

This application claims priority to U.S. Provisional Patent Application Ser. No. 61/533,447, filed Sep. 12, 2011, the disclosure of all of which is incorporated herein by reference in its entirety.

FIELD OF THE INVENTION

This invention relates to devices for in-situ sampling of hydrocarbon containing reservoirs, more particularly to nanostructured devices for the in-situ sampling of hydrocarbon containing reservoirs for providing information regarding composition or properties of fluids contained therein.

BACKGROUND OF THE INVENTION

Crude oil is the world's main source of hydrocarbons that are used as transportation fuel and petrochemical feedstock. One overriding problem in exploring for hydrocarbons in the subsurface is the probing and characterization of an environment that cannot be seen. Similarly, after a hydrocarbon reservoir or deposit has been discovered and is ready to be developed and exploited, many assumptions must be made by reservoir geologists and reservoir engineers regarding the hydrocarbons present in the reservoir. Many unknowns still exist during secondary and tertiary production.

Present technology does not provide adequate methods for the in-situ sampling of fluids contained in hydrocarbon reservoirs. Current methods require that fluids be produced from a borehole in the reservoir before they can be fully analyzed. Knowledge of the composition and the properties of the reservoir fluids within the reservoir well away from the borehole, even rough approximations, would be invaluable. Variables of interest include, but are not limited to, pH, salinity, $H_2S$ concentration, ion fractions, and dissolved hydrocarbon concentration and composition. Thus, there exists a need to provide devices capable of the in-situ sampling of hydrocarbon reservoirs well away from the borehole.

Nanotechnology brings new and different possibilities into upstream exploration, detection, and production. In general, the industry desires strong, stable, friction resistant, and corrosion combatant materials in virtually all of its operations and processes, including sampling devices. These requirements can be favorably addressed with a bottom-up approach for material design and fabrication, and by employing nanofabricated particles for use in drilling, completion, stimulation, and injection fluids. Indeed, nanostructured components are becoming increasingly attractive for traversing the native pore structure of reservoir rock and generating information about the mid reservoir environment.

As recovery of worldwide petroleum reserves becomes increasingly difficult, methods for the in-situ detection and sampling of petroleum reservoirs becomes more and more critical. Due to the high pressures and temperatures that are encountered in subsurface formations, materials that are able to withstand these conditions are needed. Thus, there is a need for the development of suitable materials for use with the mapping of petroleum reservoirs.

SUMMARY

This invention relates to nanostructured devices for the in-situ sampling of hydrocarbon containing reservoirs. Provided herein is a nanostructured sampling device that can be deployed within and transported through a hydrocarbon reservoir using a carrier fluid. The carrier fluid can be any fluid that is compatible with the reservoir and the reservoir fluid. Preferred carrier fluids include water or brine, such as can be injected in secondary recovery, pressure maintenance, or water-flood production of oil. The fluid samples that are captured by the device can then be analyzed after the retrieval of the device from fluids produced from the reservoir. The injection and/or carrier fluids can also include certain surfactants, salts and other agents for modifying reservoir and fluid properties (e.g., viscosity, interfacial tension, wettability, and the like).

In one aspect, an in-situ fluid sampling device for deployment within a hydrocarbon containing reservoir is provided. The fluid sampling device includes a porous anodic alumina substrate; and an erodible coating applied to the surface of the porous anodic alumina substrate such that the erodible coating covers the openings of the pores in the substrate, wherein the erodible coating is operable to erode in the presence of hot water, thereby exposing the pores of openings the substrate. To subsequently seal the pores in the anodic alumina substrate, the anodic alumina can be contacted with water at a temperature of about 100° C. or greater.

In another aspect, a method for preparing an in-situ fluid sampling device for deployment within a hydrocarbon containing reservoir is provided. The method includes the steps of providing a porous anodic alumina film; and applying an erodible coating over pores within the porous anodic alumina film to provide a coated anodic alumina film In another aspect, a method for the in situ fluid sampling of a hydrocarbon subterranean reservoir is provided. The method includes the steps of injecting a plurality of nanostructured sampling devices disposed in a carrier fluid into a hydrocarbon containing subterranean reservoir, wherein the carrier fluid is selected from the group consisting of water, brine, drilling fluids, fracturing fluids, stimulation fluids, and the like. The device includes a porous anodic alumina substrate; and an erodible coating applied to the surface of the porous anodic alumina substrate such that the erodible coating covers the pores of the substrate, wherein the erodible coating is operable to erode in the presence of hot water, thereby exposing the pore openings of the substrate. The method of sampling fluids includes the step of causing the sampling devices to enter the hydrocarbon reservoir. After a certain amount of time within the reservoir, the fluids contained in the subterranean reservoir erodes the coating on the surface of sampling device erodes, thereby exposing the pores. Collection of fluid samples, including entrained and dissolved hydrocarbons, within the pores of the device begins as fluid samples enter the pores of the sampling device. The method includes trapping the reservoir fluid samples within the devices by allowing the pore aperture to swell upon prolonged contact with hot water or brine within the reservoir. The pore openings of the substrate swell, thereby trapping the reservoir fluid samples therein; and recovering the devices with the reservoir fluid samples therein.

DETAILED DESCRIPTION OF THE INVENTION

Although the following detailed description contains many specific details for purposes of illustration, it is understood that one of ordinary skill in the art will appreciate that many examples, variations and alterations to the following details are within the scope and spirit of the invention. Accordingly, the exemplary embodiments of the invention described herein are set forth without any loss of generality, and without imposing limitations, relating to the claimed invention.

Herein is provided a novel sampling device that can be deployed within and transported through a hydrocarbon reservoir using a carrier fluid. The carrier fluid can be any known fluid typically associated with the production or recovery of hydrocarbons from subsurface reservoirs, such as injected water or brines, such as can be used in secondary, or waterflood production of oil or water or brine laded with agents for modifying surface tension or wettability, such as are used in tertiary or enhanced oil recovery. Other fluids can include drilling fluids, fracturing fluids, and stimulation fluids. Upon injection, the carrier fluid will mix with native reservoir fluids, especially the connate water. Injected fluids, in general, are injected at much lower temperatures than are found in the reservoir (i.e., fluids are injected at temperatures of between about 20 and 50° C.), and the erodible coatings on the injected devices will generally be breached and begin sampling after some period of time. The injected device will primarily capture connate water, partially diluted with the injection fluid. The connate water naturally includes dissolved and suspended hydrocarbons that are representative of the hydrocarbon reserve contained in the reservoir. Some of the pores of the device will also capture undiluted petroleum samples if the pore openings get exposed while in contact with the liquid hydrocarbon. The likelihood of direct contact with a hydrocarbon droplet or sample in the reservoir may, in certain embodiments, be influenced by the presence and selection of appropriate coatings on the device. In general, the fluids are injected into the reservoir through an injection well, and are recovered at an adjacent production well, thereby achieving cross-well sampling. Within the reservoir, the sampling device captures reservoir fluids, including connate water and hydrocarbons, which are then analyzed after the retrieval of the sampling devices from fluids produced from the reservoir. Single-well sampling may also be performed, for example, by injecting devices into a given well, leaving the devices in place for given period of time, and then retrieving the devices from fluids produced from the same well.

Porous Anodic Alumina

Anodic alumina is a self-organized nanostructured material that includes a high density of uniform cylindrical pores throughout that are aligned perpendicular to the surface of the materials and penetrate its entire thickness. In certain preferred embodiments, the cylindrical pores penetrate the majority of the anodic alumina without completely penetrating the structure, thereby providing a structure that has cavities formed therein. Under certain conditions, a regular porous structure can be formed when aluminum is electrochemically oxidized (anodized) in certain specific solutions. In these materials, a thin, dense alumina barrier layer separates the pores from the aluminum.

The anodic aluminum oxide (AAO) templates that form the building block of the present devices that are prepared by self-assembly during electrochemical oxidation of aluminum bulk, coatings, or thin films. In certain embodiments, the self assembly process produces a substrate that has pores that can be approximately 30 nm wide that are spaced approximately 60 nm apart. In certain embodiments, the pores can form an approximately hexagonal close-packed arrangement. The pore diameter of the porous anodic alumina can be tuned from between about 5 nm and 300 nm, alternatively between about 5 and 100 nm, alternatively between about 10 and 200 nm, alternatively between about 10 and 100 nm, or alternatively between about 100 and 250 nm One exemplary device can be prepared from an AAO sheet about 60 microns thick and pores about 60 microns long. The porous anodic alumina can have a pore density ranging from about $10^{13}$ to $10^8$ cm$^{-2}$, alternatively between about $10^{12}$ to $10^9$ cm$^{-2}$, alternatively between about $10^{11}$ to $10^9$ cm$^{-2}$, or alternatively $10^{12}$ to $10^{10}$ cm$^{-2}$. Dimensions of this porous structure are typically determined by the specific synthetic conditions that are employed, thereby providing a convenient way to precisely engineer the desired nanoscale morphology of the porous anodic alumina. In one embodiment of the present invention, the diameter of the pores can be controlled during growth by varying the anodization conditions, such as by changing the voltage applied during the etching process, as is known in the art.

The thickness or maximum dimension or diameter of the anodic aluminum oxide (AAO) substrate can be between about 100 nm and about 2000 nm, alternatively between about 250 and 1500 nm, alternatively between about 500 and 1000 nm. Additionally, almost any shape can be used for the AAO, including round, cubic, elongated, prismatic, asymmetric, and cylindrical shapes. In general, both the size and shape of the AAO substrate is dictated by the particular location where it will be deployed, and the size of the passages into which it will be injected and through which it must travel.

AAO is generally optically transparent, electrically insulating, thermally and mechanically robust, and chemically inert. The processing of AAO is compatible with microfabrication and is scaleable to high volume production. Synkera Technologies, Inc. is one exemplary provider of AAO substrates having the capabilities to engineer and produce AAO materials having nanoscale dimensions. Materials can be produced having pore diameters ranging from about 3 to 300 nm, alternatively between about 5 and 200 nm, alternatively between about 5 and 100 nm, alternatively between about 5 and 75 nm, alternatively between about 10 and 50 nm, alternatively between about 50 and 250 nm. Additionally, materials can be produced having pore lengths ranging between about 0.1 and 300 μm, alternatively between about 0.1 and 200 μm, alternatively between about 0.1 and 100 μm, alternatively between about 0.5 and 100 μm, or alternatively between about 1 and 100 μm.

The empty pore volume of the uncoated AAO structure available for fluid sampling can be between about 20 and 35% by volume of the total volume of the device, alternatively between about 25 and 32% by volume, alternatively between about 30 and 35% by volume, alternatively between about 29 and 32% by volume. In certain embodiments, the empty pore volume of the uncoated AAO structure is between about 20 and 30% by volume of the total volume of the device, alternatively between about 25 and 35% by volume.

Different architectures of AAO can also developed and are within the scope of the invention and used the for the present invention, for example, AAO that is attached to Al foil, freestanding AAO wafers, and AAO nanotemplates integrated onto various non-aluminum substrates, such as silicon wafers, plastic, ceramic, metal and glass, to name a few.

Erodible Coatings

Erodible coatings can be applied to the surface of the AAO substrate to function as time-release agents. The time-release coatings rely upon their dissolution and/or decomposition rates under known conditions, which are typically fairly low rates. For example, ester bonds hydrolyze in physiological saline at body temperature at a useful rate, and are thus useful for use in biomedical devices, for example, as experienced with polyethylene terephthalate. Other materials that can be useful for controlled erosion/dissolution can include: cellulose, polyoxyethylene, polyacrylate, a copolymer of acrylate and methacrylate, a methacrylate polymer, a copolymer of acrylate and methacrylate, a copolymer of acrylate and methacrylate with ammonium group, a copolymer of maleic anhydride and methyl vinyl ether, hydroxy propyl ethyl cellulose, hydroxy propyl cellulose, hydroxy ethyl cellulose, methyl cellulose, hydroxymethyl methacrylate, maltodextrin, natural gum and xanthan gum. In certain embodiments, polyamides can be used as the erodible coating, as the amide bonds hydrolyze slowly under reservoir conditions. One exemplary polyamide is Nylon-66. Materials used to form the erodible coating can be organic or inorganic materials, having either covalent or ionic bonding, and in certain embodiments can be polymeric materials or can be salts.

Application of the erodible coating to prepare the coated alumina materials can be done by various deposition or coating means, such as electrodeposition, polymerization, sol-gel chemistry, chemical vapor deposition (CVD), spin coating, spray coating, slot coating, dip coating, screen printing, lamination, ink jet printing, offset printing, roll coating, falling film coating, sputtering, thermal evaporation, as well as other known methods. Such methods are known in the art. In one embodiment, a viscous mixture can be prepared that includes a primary resin, and a hardener and the viscous mixture can then be coated onto the surface of the AAO substrate. Exemplary hardeners can include bisphenol-A, epichlorohydrin, and like compounds. Preferably the coating thickness is between about 50 and 150 nm, alternatively between about 75 and 125 nm, alternatively between about 90 and 110 nm. In preferred embodiments, the coating does not enter and fill the pores in the substrate. The process steps for preparing the devices described herein include steps used in micromachining, including process steps of thin film deposition, photolithography and etching. While each coating method has particular advantages, in certain embodiments, sputtering is preferred for the application of inorganic materials and spin coating is preferred for organic materials. Organic materials can be applied with or without dilution into a carrier fluid.

In certain embodiments, the device according to the present invention includes a porous anodic alumina substrate having a plurality of elongated pores and an erodible coating applied to the exterior surface of the substrate. The overall dimensions of the device can be selected to specifically fit into the spaces within the rock matrix of the hydrocarbon reservoir, which can range from between about 1 μm and 1 mm For example, if devices are deployed in oolitic limestone, desired dimensions range from between about 0.1 μm and 10 μm, alternatively between about 0.2 μm and 2 μm, alternatively between about 1 μm and 4 μm. If the devices are deployed in a natural or hydraulic fracture, device dimensions up to about 1 millimeter, alternatively up to about 0.5 mm, alternatively up to about 0.1 mm are desired. The device can be injected into and carried throughout the reservoir, preferably while suspended in an injected carrier fluid.

In certain embodiments, and under certain reservoir conditions, the erodible coating is operable to erode over a pre-defined period of time between about 0.5 days and 1 month, alternatively between about 0.5 days and 3 days, alternatively between about 1 day and 1 week, alternatively between about 1 week and 2 weeks, alternatively between about 2 weeks and 4 weeks. In certain embodiments, the erodible coating is operable to erode over a pre-defined period of time greater than about 1 month. In certain embodiments, the erodible coating erodes over a period of about 3 months, alternatively over a period of about 6 months, alternatively over a period of about 12 months, alternatively over a period of about 24 months, alternatively over a period of about 36 months, upon exposure to the reservoir conditions.

The rate at which the coating erodes is dependent primarily upon the material, and the thickness of the coating, reservoir temperature, and fluid chemistries. In certain embodiments, the coating can be stable in water at room temperature, but will begin to dissolve in water or brine solutions at temperatures of at least about 50° C., alternatively at least about 70° C., alternatively at least about 90° C., alternatively at least about 100° C., alternatively at least about 110° C., alternatively at least about 120° C. In certain embodiments, the speed at which the coating erodes increases with increasing temperature of the reservoir. For example, in certain embodiments, rate at which the coating erodes generally increases by a factor of two for every increase in temperature of about 10° C.

The erodible coating preferably has a thickness of between about 10 and 500 nm, alternatively between about 25 and 250 nm, alternatively between about 25 and 100 nm, alternatively between about 50 and 150 nm, alternatively between about 100 and 200 nm. The thickness of the erodible coating is determined relative to the desired rate of erosion, and the location within the hydrocarbon reservoir that is desired to be sampled.

Passivation Coatings

In certain embodiments, the device can optionally include a passivation coating applied to the erodible coating that is operable to minimize flocculation and sedimentation and to reduce or prevent adhesion to surfaces in the reservoir. Generally, such coatings include polymeric materials and the polymeric passivation coating does not itself erode or degrade by design when the coated particles are placed within the reservoir. Exemplary polymeric passivation coatings can include polyethylene glycol, PEO (polyethylene oxide) and PPO (polypropylene oxide) copolymers, poly betaines, polystryene sulfonate, and other like polymers In certain embodiments, the passivation coatings can be an inorganic material that has been selected to provide a desired surface charge under reservoir conditions, for example, at a given pH, temperature and/or salinity. The passivation coatings can, in certain embodiments, encapsulate all of the exterior surfaces of the sampling devices, for devices wherein the surface includes the erodible coating and surfaces wherein the native anodic alumina is exposed. When the exterior surface is coated with the passivation coating, a small fraction of the overall device surface includes an erodible coating, typically about 16% if the device is generally cubic in shape, and the pores are open at only one end.

The thickness of the optional polymeric passivation coating for minimizing flocculation and sedimentation and reducing or preventing adhesion is typically thin, for example less than about 50 nm, alternatively less than about 25 nm, alternatively less than about 10 nm, alternatively less than about 5 nm, alternatively between about 1 and 5 nm.

In applying the polymeric passivation coating for minimizing flocculation and sedimentation and reducing or preventing adhesion, the erodible coating is typically allowed to dry prior to application thereof. In certain embodiments, drying can be enhanced or improved by heating the device, either in air or under an inert atmosphere.

In certain embodiments, the polymeric passivation coating for minimizing flocculation and sedimentation and reducing or preventing adhesion can be chemically attached to either exposed sides or the surfaces of the AAO substrate or the erodible coating. In these embodiments, the polymeric passivation coating can be applied to the sides of the AAO, where, for example, the erodible coating has not been applied. For example, carboxylic acids can be useful for attaching organic compounds to alumina. Alternatively, block copolymers chemistry can be used to graft the polymer passivation coating to the erodible coating.

Sample Capture

The porous AAO substrate can be coated with an erodible coating disposed on the surface thereof, thereby allowing for programmable sampling of a reservoir. For example, by knowing the rate at which the erodible coating will erode from the surface of alumina base, sampling of the reservoir can be programmed.

In certain embodiments, the devices described herein can be injected into a reservoir via an injection well, and can be recovered via a production well. Alternatively, the devices described herein can be injected and recovered from the same well.

After the erodible coating has been removed, the reservoir fluids that are being sampled can enter the pores of the alumina substrate. Upon exposure to the hot water, the pore openings swell, effectively sealing the captured fluids in the alumina. In certain embodiments, the temperature of the water causing the pore openings to swell is near or greater than the boiling point of water, for example, at least about 85° C., alternatively at least about 90° C., or alternatively at least about 100° C. Typically, upon exposure to water or brine at a temperature of about 100° C. for at least about 20 min., alternatively at least about 30 min., the pores will swell to the point that molecules of the sampled fluids are trapped therein. It is understood that at lower temperatures, increased time of exposure of the water or brine may be necessary to close the pores of the substrate, for example approximately 40 minutes at about 90° C., alternatively at least about 80 minutes at a temperature of about 80° C., alternatively at least about 160 minutes at a temperature of about 70° C., or alternatively at least about 320 minutes at a temperature of about 60° C., and that at greater temperatures, decreased exposure time may be necessary. At lower temperatures, additional time may be needed to cause the pores in the substrate to swell and trap the fluids therein.

In certain embodiments, the thickness of the erodible cap can be selected such that sampling of the reservoir can occur at an approximately pre-determined time. More specifically, the material that is used for the erodible cap can be selected based upon a known and desired erosion rate in the fluid medium, which will usually be hot brine. Upon erosion of the capping material, the host fluid medium, including the hydrocarbons being sampled, diffuses into and fills one or more of the exposed pores. After a period of time, the medium, for example hot water or brine, causes swelling and closure of the pore, effectively locking the fluid sample inside the pore. The amount of time, as noted previously, is dependent upon the temperature of medium. The device can be retrieved from the reservoir and analyzed to determine the composition and properties of the captured fluids.

AAO is typically produced from thin sheets of high purity aluminum, or alternatively from thin films of aluminum on a carrier substrate. Free-standing AAO sheets can then be detached from the carrier or substrate by chemical etch, as is described in the literature.

Sampling devices can be produced from AAO sheets by adding a layer of erodible capping material, and then dividing the AAO material into pieces. The division may be accomplished by a number of means, including simply breaking the sheet into smaller fragments, sawing, crushing or cutting.

In other embodiments, the capping material can be applied to the AAO sheets by a number of means, including spin-coating, spray coating, screen printing, electrospraying, inkjet printing, and the like. In embodiments wherein the capping agent has been deposited in uniform droplets to form a discontinuous film, e.g., by inkjet or electrospray, these droplets can be used as selective mask (similar to how a resist functions) for the wet or dry etching of the alumina and direct formation of the sampling devices.

When deployed into a hydrocarbon containing reservoir, a variety of devices according to the present invention having different thicknesses of capping material can be used to sample reservoir fluids at a variety of times after injection. Similarly, if a single sampling device is provided having a capping layer having a variable thickness at different locations over the surface of the device (for example, a dome or wedge, in cross section), the pores will be activated and will sample the reservoir at different times. The recovered device can be sampled, such as by microprobe means (e.g., SEM with EDAX), to analyze the captured fluids in the different pores, which can then be correlated to different locations within the hydrocarbon reservoir.

Recovery

Recovery of the sampling devices of the present invention, particularly the AAO materials having sampled reservoir fluids trapped therein, can be achieved by filtration or sedimentation. In one aspect, the sampling devices described herein are designed to be injected into a water flooded reservoir for determination of the residual materials present in the field. Filtration means can be employed that include agitators and filtering means. In one embodiment, magnetic particles can be attached to the substrate materials to facilitate separation by magnetic means. For example, a polymer coating can be applied to the AAO substrate that includes superparamagnetic oxide particles chelated onto it, thereby allowing for the use of magnetic separation techniques. Such superparamagnetic particles are known for the extraction of bio-agents.

The sampling devices having the reservoir fluids can be analyzed by mechanically crushing the devices to release the fluids trapped therein. In one embodiment, a ball mill, press or pliers can be used to grind and/or crush the devices for analysis of the fluids trapped therein. In an alternate embodiment, a focused ion beam, used in conjunction with an SEM can be used to release the fluids for analysis thereof.

Method of Preparation of Device

In one aspect of the present invention, a method for preparing the sampling devices described herein is provided. The method includes the steps of providing an AAO membrane having a thickness of between about 450 nm and 550 nm, preferably, in this embodiment, having a thickness of about 500 nm. The AAO membrane can have pores between about 30 and 60 nm in diameter, preferably, in this example, having a diameter of about 50 nm. The pores are preferably formed such that they are closed on one end, i.e., such that one side is open and one side is closed. The membrane can be of any size, such as for example, a square having side dimensions of about 10 cm.

The AAO membrane can then be coated with the erodible coating that will serve as a cap for the pores. Exemplary materials can include polymeric thermoset resins, such as Nylon-66, an aromatic polyamide to provide an erodible coating having a thickness of about 100 nm, which preferably does not enter into the pores of the substrate. The coating is allowed to cure and harden.

The coated AAO membrane can then be prepared into separate pieces of the desired size. For example, in one embodiment, this can be accomplished by lithographic means, such as by using a resist layer and isotropic etch. Such methods utilizing lithography are known to those of skill in the art for the preparation of integrated circuits and micromachines. In an alternate embodiment, the coated membrane can be crushed into particles having a diameter of less than about 1 μm. When utilizing the crushing procedure to prepare devices, the crushing is preferably done at low, or relatively low, temperature to ensure the erodible coating layer is brittle. Sieves can be utilized to recover particles of a desired size, such as for example, particles having a maximum dimension of 1 μm.

Particles can be further separated by floatation, which can separate particles having air trapped within the pores from particles having the erodible coating trapped within the pores. Liquids having an appropriate density can be selected to facilitate separation of the particles. The separated particles can then be rinsed and dried.

Optionally, the coated AAO particles can further be coated with a polymeric passivation coating to optimize suspension is brine, and to minimize flocculation when the particles are suspended in injection and/or reservoir fluids. Because carboxylic moieties are known to chelate to aluminum oxide surfaces, and because poly(ethyleneglycol) (PEG) is a known suspension agent, the coated AAO particles can be further coated with carboxylic acid functionalized PEG molecules (PEG-COOH). The PEG-COOH coating can be applied by first dissolving the PEG-COOH in water, and then immersing the coated AAO particles in the solution. Following treatment, the particles can be rinsed with water and dried.

Although the present invention has been described in detail, it should be understood that various changes, substitutions, and alterations can be made hereupon without departing from the principle and scope of the invention. Accordingly, the scope of the present invention should be determined by the following claims and their appropriate legal equivalents.

The singular forms "a", "an" and "the" include plural referents, unless the context clearly dictates otherwise.

Optional or optionally means that the subsequently described event or circumstances may or may not occur. The description includes instances where the event or circumstance occurs and instances where it does not occur.

Ranges may be expressed herein as from about one particular value, and/or to about another particular value. When such a range is expressed, it is to be understood that another embodiment is from the one particular value and/or to the other particular value, along with all combinations within said range.

Throughout this application, where patents or publications are referenced, the disclosures of these references in their entireties are intended to be incorporated by reference into this application, in order to more fully describe the state of the art to which the invention pertains, except when these references contradict the statements made herein.

That which is claimed is:

1. An in-situ fluid sampling device for deployment within a hydrocarbon fluid containing reservoir, the device comprising:
   a porous anodic alumina substrate;
   an erodible coating applied to the surface of the porous anodic alumina substrate such that the erodible coating covers the pores of the substrate, wherein the erodible coating is operable to erode in the presence of hot water, thereby revealing the pores of the substrate; and
   a polymeric passivation coating applied over the erodible coating, the polymeric passivation coating is operable to erode in the presence of hot water, thereby revealing the erodible coating there beneath.

2. The in-situ fluid sampling device of claim 1 wherein the pores of the substrate swell in the presence of hot water, thereby trapping fluids within the pore.

3. The in-situ fluid sampling device of claim 1 wherein the porous anodic alumina substrate comprises a plurality of pores having pore diameters ranging between about 5 and 200 nm, and a length of between about 0.5 and 100 μm.

4. The in-situ fluid sampling device of claim 1 wherein the erodible coating is selected from the group consisting of cellulose, derivatives of cellulose, polyoxyethylene, polyacrylate, copolymers of acrylate and methacrylate, and combinations thereof.

5. The in-situ fluid sampling device of claim 1 wherein the erodible coating has a thickness of between about 50 and 150 nm.

6. The in-situ fluid sampling device of claim 1 wherein the erodible coating erodes when in contact with hot water or brine within the reservoir at a rate of between about 3 days and 3 weeks.

7. The in-situ fluid sampling device of claim 1 wherein the polymeric passivation coating is Nylon-66.

8. The in-situ fluid sampling device of claim 1 wherein the polymeric passivation coating has a thickness of less than about 10 nm.

9. A method for the in situ sampling of fluids in a hydrocarbon containing subterranean reservoir, the method comprising the steps of:
   injecting a plurality of sampling devices according to claim 1 disposed in a carrier fluid into the hydrocarbon containing subterranean reservoir, wherein the carrier fluid is selected from the group consisting of water and brine;
   allowing the sampling devices to enter the hydrocarbon containing subterranean reservoir, wherein fluids contained in the subterranean reservoir erode the erodible coating from the surface of the sampling device;
   collecting fluid samples within the devices, wherein upon the erosion of the erodible coating from the surface of the sampling device, the pores in the alumina are exposed, thereby allowing for fluid samples to enter said pores;
   trapping the fluid samples within the devices by allowing the substrate to swell upon prolonged contact with water or brine within the reservoir, wherein upon said prolonged contact, the pores swell, thereby trapping the fluid samples therein; and
   recovering the devices with the fluid samples therein.

10. A method for preparing an in-situ fluid sampling device for deployment within a hydrocarbon containing reservoir, the method comprising the steps of:
    providing a porous anodic alumina film;
    applying an erodible coating over pores within the porous anodic alumina film to provide a coated anodic alumina film; and
    applying a polymeric passivation coating to the coated anodic alumina film.

11. The method of claim 10 further comprising the step of preparing individual devices having a maximum dimension of not greater than about 100 nm from the coated anodic alumina film.

12. The method of claim 10 wherein the porous anodic alumina film includes pores that extend into one side of the film, but do not extend through the film.

13. The method of claim 10 wherein the polymeric passivation coating is Nylon-66.

14. A method of claim 10 wherein the erodible coating is applied to the porous anodic alumina film by spin coating, spray coating, dip coating, roll coating, sputtering, thermal evaporation, screen printing, electrospraying, electrodeposition, lamination, offset printing or ink jet printing.

* * * * *